(12) United States Patent
Oda et al.

(10) Patent No.: US 7,425,559 B2
(45) Date of Patent: Sep. 16, 2008

(54) MEDICINE CONTAINING PYRIMIDINE DERIVATIVE

(75) Inventors: Tomiichiro Oda, Tokyo-to (JP); Shigeko Uryu, Tokyo-to (JP); Shinya Tokuhiro, Tokyo-to (JP)

(73) Assignee: BTG International Limited, London (GB)

( * ) Notice: Subject to any disclaimer, the term of this patent is extended or adjusted under 35 U.S.C. 154(b) by 309 days.

(21) Appl. No.: 10/483,674

(22) PCT Filed: Jul. 11, 2002

(86) PCT No.: PCT/JP02/07060

§ 371 (c)(1), (2), (4) Date: Jun. 29, 2004

(87) PCT Pub. No.: WO03/006024

PCT Pub. Date: Jan. 23, 2003

(65) Prior Publication Data

US 2004/0242605 A1 Dec. 2, 2004

(30) Foreign Application Priority Data

Jul. 13, 2001 (JP) ............................... 2001-213338

(51) Int. Cl.
*A61K 43/54* (2006.01)
*C07D 239/42* (2006.01)
*C07D 401/04* (2006.01)
*A01N 43/58* (2006.01)

(52) U.S. Cl. ...................................... 514/256; 514/247
(58) Field of Classification Search ................. 514/183, 514/247, 256
See application file for complete search history.

(56) References Cited

U.S. PATENT DOCUMENTS

| 4,007,189 | A | 2/1977 | Sato et al. | |
| 6,245,769 | B1 * | 6/2001 | Arvanitis et al. | 514/228.5 |

FOREIGN PATENT DOCUMENTS

| EP | 0 347 252 A2 | 12/1989 |
| EP | 0 369 145 A2 | 5/1990 |
| EP | 0 945 442 A1 | 9/1999 |
| EP | 0 945 443 A1 | 9/1999 |
| EP | 1 238 979 A1 | 9/2002 |
| EP | 1 245 567 A1 | 10/2002 |
| EP | 1 266 649 A1 | 12/2002 |
| JP | 51-141896 A | 12/1976 |
| JP | 52 116497 | 9/1977 |
| JP | 52-116497 A | 9/1977 |
| JP | 53 53697 | 5/1978 |
| JP | 53053698 | 5/1978 |
| JP | 53 68800 | 6/1978 |
| JP | 56 49385 | 5/1981 |
| JP | 56 49391 | 5/1981 |
| JP | 57 35593 | 2/1982 |
| JP | 2-76880 A | 3/1990 |
| JP | 10 120683 | 5/1998 |
| WO | WO 83/02944 | 9/1983 |
| WO | WO 98/33799 | 8/1998 |
| WO | WO 00/40561 | 7/2000 |
| WO | WO 01/42247 A1 | 6/2001 |
| WO | WO 02/053526 | 7/2002 |
| WO | WO 02/058697 | 8/2002 |

OTHER PUBLICATIONS

Scatena R., et al. "An update on pharmacological approaches to neurodegenerative diseases," Expert Opin. Investig. Drugs 2007 16(1):59-72.*

Rogers J., et al., "Neuroinflammation in Alzheimer's Disease and Parkinson's Disease: are microglia pathogenic in either disorder?" Aug. 2007 Int. Review of Neurobiology vol. 82: abstract only.*

Suh, Myung Eun, et al; "Novel Synthesis of 8-tert-Butyl-6,7-Dihydro-5-Methyl-8H-Pyrrolo [3.2-3]-s-Triazolo-[1,5-a] Pyrimidine (Bumepidil), a New Cardiovascular Agent"; *College of Pharmacy, Ewha Women's University*; 31(5); pp. 338-342 (1987).

Motomura, S., et al; "Characterization of Cardiovascular Actions of CS-611, a New Coronary Dilator, in the Dog"; *Arzneimittel-Forschung, Drug Research*; 31(8); pp. 1238-1244 (1981).

Kumakura, S., et al; "Cardiovascular Pharmacology of Bumepidil, a New Synthetic Vasoactive Compound for Coronary Circulation"; *Arzneimittel-Forschung, Drug Research*; 31(5); pp 785-790 (1981).

Yasunobu, S., et al; "Studies on Cardiovascular Agents. 6. Synthesis and Coronary Vasodilating and Antihypertensive Activities of 1,2,4-triazolo[1,5-a]Pyrimidines Fused to Heterocyclic Systems"; *Journal of Medicinal Chemistry*; 23(8), pp. 927-937 (1980).

(Continued)

*Primary Examiner*—Ardin Marschel
*Assistant Examiner*—Amy A Lewis
(74) *Attorney, Agent, or Firm*—Nixon & Vanderhye

(57) ABSTRACT

A medicine for central diseases which contains as the active ingredient either a compound represented by the general formula (I): (I) (wherein $R^1$ represents hydrogen or $C_{1-6}$ alkyl; $R^2$ represents $C_{1-6}$ alkyl, etc.; A represents carbon, etc.; D represents $C_{1-6}$ alkylene, etc.; E represents carbon, etc.; and Arom represents aryl, etc.) or a pharmacologically acceptable salt of the compound.

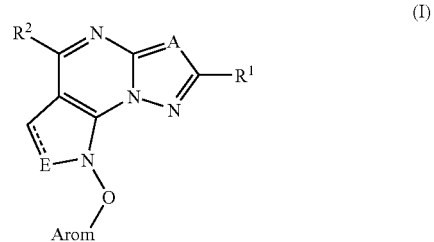

(I)

14 Claims, No Drawings

OTHER PUBLICATIONS

Ito, K., et al; "Effects of CS-611 on the Electrophysiological Properties of Canine Cardiac Tissues"; *Archives Internationales de Pharmacodynamie et de Therapie*; 244(1); pp. 73-85 (1980).

Ebihara, A., et al; "Pharmacokinetics and Pharmacodynamics of the Vasodilator CS-611 in Humans"; 10(1); pp. 89-90 (1979).

Nadhim Bayatti et al; "The neuroprotective actions of corticotrophin releasing hormone" Ageing Research Review, 4 (2005) 258-270.

Domenico Marco Bonifatiet al; "Role of complement in neurodegeneration and neuroinflammation" Molecular Immunology, 44 (5) 999-1010, 2007 (EPUB May 15$^{th}$, 2006).

Donald R Gehlert et al; "3-(4-Chloro-2-Morpholin-4-ylThiazol-5-yl)-8-(1-Ethylpropyl)-2,6-Dimethyl-Imidazo[1,2-b]Pyridazine:A Novel Brain-Penetrant, Orally Available Corticotropin-releasing Factor Receptor 1 Antagonist with Efficacy in Animals Models of Alcoholism" The Journal of Neuroscience, Mar. 7, 2007, 27(10) 2718-2726.

Alexander Gerhard et al; "In vivo imaging of microglial activation with [$^{11}$C](R)-PK11195 PET in idiopathic Parkinson's disease", Neurobiology of Disease 21 (2006) 404-412.

Paul J Gilligan et al "Corticotropin-releasing factor receptor antagonists", Expert Opin. Ther.Patents (2006) 16(7): 913-924.

E Hansson "Could chronic pain and spread of pain sensation be induced and matained by glial activation?", Acta Physiol 2006, 187, 321-327.

Shawn Hayley et a; "Multiple Mechanisms of Cytokine Action in Neurodegenerative and Psychiatric States: Neurochemical and Molecular Substrates"., Current Pharmacejutical Designs 2004, 11, 947-962.

Katia Karalis et al; "Autocrine or Paracrine Inflammatory Actions of Corticotropin-Releasing Hormone in Vivo", Science. vol. 254, Issue 5040, 421-423.

Yasuomi Ouchi et al; "Microglial Activation and Dopamine Terminal Loss in Early Parkinson's Disease", Ann Neurol 2005; 57; 168-175.

Emma Schofield et al; "Severity of gliosis in Pick's disease and frontotemporal lobar degeneration: tau-positive glia differentiate these disorders",Brain (2003), 126, 827-840.

Myung Eun Suh et al "8-tert-Butyl-6,7-Dihydro-5-Methyl-8H-Pyrrolo [3,2-e]-s-Triazolo-[1.5-a] Pyrimidine (Bumepidil)", Yakhak Hoeji Vo. 31, No. 5 338-342 (1987).

Peter Teismann et al "Cellular pathology of Parkinson's disease: astrocytes, microglia and inflammation", Cell Tissue Res (2004) 318, 149-161.

Theoharis C. Theoharides et al; "Corticotropin-Releasing Hormone Induces Skin Mast Cell Degranulation and Increased Vascular Permeability, A possible explanation for its proinflammatory effects", Endocrinology 139; 403-413, 1998.

Shigeko Uryu et al: "β-Amyloid-specific upregulation of stearoyl coenzyme A desaturase-1 in macrophages", Biochemical and Biophysical Research Communications 303 (2003) 302-305.

P J Whitehouse et al; "Reductions in corticotrophin releasing factor-like immunoreactivity in cerebral cortex in Alzheimer's disease, Parkinson's disease, and progressive supranuclear palsy", Neurology 1987: 37: 905-909.

Brandy Wilkinson et al; "Fibrillar Beta-Amyloid stimulated intracellular signaling cascades require vav for induction of respiratory burst and phagocytosis in monocytes and microglia", J. Biol. Chem. Jul. 2006, 281: 20842-20850 (E-Pub 25$^{th}$ May 2006).

Marcin Wojtera et al; "Microglial cells in neurodegenerative disorders"; Folia Neuropathol 2005; 43 (4) 311-321.

Katia Karalis et al; "Autocrine or Paracrine Inflammatory Actions of Corticotropin-Releasing Hormone in Vivo", Science. vol. 254, Issue 5040, 421-423 , Oct. 1991.

* cited by examiner

MEDICINE CONTAINING PYRIMIDINE DERIVATIVE

This application is the U.S. National Phase of International Application PCT/JP02/07060, filed 11 Jul. 2002, which designated the U.S.

TECHNICAL FIELD

The present invention relates to a drug for central diseases (particularly Alzheimer's disease), or a drug for Alzheimer's disease where microglia are activated (particularly those where microglia are activated by β-amyloid), in which a pyrimidine derivative is the active component; a method for the treatment of central diseases (particularly Alzheimer's disease) or Alzheimer's disease where microglia are activated (particularly where microglia are activated by β-amyloid) in which a pyrimidine derivative is used; and the use of a pyrimidine derivative to produce a drug for central diseases (particularly Alzheimer's disease) or a drug for Alzheimer's disease where microglia are activated (particularly those where microglia are activated by β-amyloid).

BACKGROUND TECHNOLOGY

Immunoglobulin, T lymphocytes and the like are not present in the central nervous system and so it is generally thought that immune reactions occur there less readily than in peripheral tissue. It has recently been reported, however, that TGF(transforming growth factor)β, IL-1, IL-6 and other such cytokines and complements have been confirmed present in geriatric maculae—one of the distinctive features of Alzheimer's disease—in addition to β-amyloid protein (Aβ), which is a main structural component thereof; that these are not brought in by peripheral blood but are produced by cells in the brain; and that immune reactions do occur even in the central nervous system. Microglia are thought to be the cells playing the main role in immune reactions in the brain. Microglia cells are present specifically in the brain, are englobing, produce and excrete various cytokines and free radicals, and so forth, and what is known of their nature to date suggests that they are similar in many respects to macrophages. With Alzheimer's disease, a strong activated microglia reaction accompanies geriatric maculae and neurofibrillary degeneration. Removal of the pathological products thereof is thought to be the original purpose of microglia activation, but geriatric maculae and the like are insoluble and therefore untreatable, and, conversely, the complements, cytokines, free radicals and the like produced by the microglia are thought to damage the surrounding neurocytes. For example, it has been reported that microglia activated in vitro by lipopolysaccharide (LPS) and cytokine produce NO and are toxic to neurocytes, or that some of the factors produced are toxic only to neurocytes and have no effect on astrocytes, oligodendrocytes or Schwann cells. There are also reports suggesting the possibility that during the formation of geriatric maculae, also, microglia contribute to the conversion and progression of diffuse plaques that are not toxic to cells, to compact plaques where the surrounding neurocytes are degenerating. Moreover, as there are reports that microglia are activated by Aβ, it has been suggested that microglia activation may be broadly related to neural degeneration in Alzheimer's disease.

It is therefore anticipated that a compound that can suppress microglia activation due to Aβ will be effective as a drug for the prevention or treatment of Alzheimer's disease.

The inventive active component is a pyrimidine derivative, and whereas it is known that pyrimidine derivatives have a vasodilatory effect and a blood pressure-lowering effect (Japanese unexamined patents S51-141896 and S52-116497, and J. Med. Chem. 1980, 23, 927-937), and that they have a beneficial effect against cachexia (Japanese unexamined patent H2-76880), their effect as a drug for central diseases is not known.

DISCLOSURE OF THE INVENTION

As a result of diligent research into the pharmacological effect of pyrimidine derivatives, the present inventors perfected the present invention upon discovering that a pyrimidine derivative or pharmacologically acceptable salt thereof acts as an excellent drug for central diseases (particularly Alzheimer's disease) and as a drug for Alzheimer's disease where microglia are activated (particularly where microglia are activated by β-amyloid). The present invention is a drug for central diseases (particularly Alzheimer's disease) and a drug for Alzheimer's disease where microglia are activated (particularly where microglia are activated by β-amyloid) which contains a compound represented by general formula (I) below, or pharmacologically acceptable salt thereof, as active component

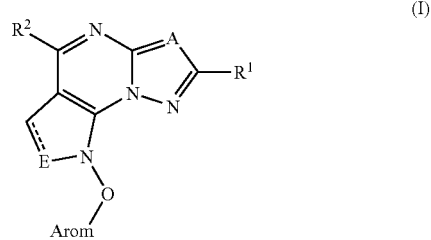

(I)

(in the formula, $R^1$ represents a hydrogen atom or $C_1$-$C_6$ alkyl group, $R^2$ represents a $C_1$-$C_6$ alkyl group or $C_3$-$C_6$ cycloalkyl group, A represents a group of formula CH, a halogen atom-substituted carbon atom or a nitrogen atom, D represents a $C_1$-$C_6$ alkylene group or halogen atom-substituted $C_1$-$C_6$ alkylene group, E represents a group of formula $CH_2$, a group of formula $CHR^3$ (in the formula, $R^3$ represents a $C_1$-$C_6$ alkyl group), a group of formula CH or a $C_1$-$C_6$ alkyl group-substituted carbon atom, Arom represents an aryl group, an aryl group having from 1 to 3 identical or different substituent groups chosen from "group α substituent groups", a heteroaryl group or a heteroaryl group having from 1 to 3 substituent groups chosen from "group α substituent groups", and the part represented by

----- is a single bond or double bond;

"group α substituent groups":

halogen atoms, $C_1$-$C_6$ alkyl groups, and $C_1$-$C_6$ alkyloxy groups).

In above-mentioned general formula (I), the "$C_1$-$C_6$ alkyl group" in $R^1$, $R^2$, E and "group α substituent groups" can, for example, be a linear or branched alkyl group of from 1 to 6 carbon atoms such as methyl, ethyl, propyl, isopropyl, butyl, isobutyl, s-butyl, t-butyl, pentyl, isopentyl, 2-methylbutyl, neopentyl, 1-ethylpropyl, hexyl, isohexyl 4-methylpentyl, 3-methylpentyl, 2-methylpentyl, 1-methylpentyl, 3,3-dimethylbutyl, 2,2-dimethlybutyl, 1,1-dimethylbutyl, 1,2-dimethlybutyl, 1,3-dimethylbutyl, 2,3-dimethylbutyl or 2-ethylbutyl, and is preferably a linear or branched alkyl group of from 1 to 4 carbon atoms, and particularly preferably a methyl group.

In above-mentioned general formula (I), the "$C_3$-$C_6$ cylcoalkyl group" in $R^2$ can, for example, be a 3 to 6-membered saturated cyclic hydrocarbon group such as cyclopropyl, cyclobutyl, cyclopentyl or cyclohexyl, and is preferably a 3 to 4-membered saturated cyclic hydrocarbon group, and particularly preferably a cyclopropyl group.

In above-mentioned general formula (I), the "halogen atom" in A, D, and "group α substituent groups" is a fluorine atom, chlorine atom, bromine atom or iodine atom, and is preferably a fluorine atom or chlorine atom.

In the above-mentioned general formula (I), the "$C_1$-$C_6$ alkylene group" in D can, for example, be a linear or branched alkylene group of from 1 to 6 carbon atoms such as methylene, methylmethylene (—CH(CH$_3$)—), dimethyl-methylene (—C(CH$_3$)$_2$—), ethylene, propylene, trimethylene, tetramethylene, 1-methyltrimethylene, 2-methyltrimethylene, 3-methyltrimethylene, pentamethylene or hexa-methylene, and is preferably a linear or branched alkylene group of from 1 to 4 carbon atoms, and particularly preferably a methylene, ethylene or methyl methylene group.

In the above-mentioned general formula (I), the "aryl group" in Arom can, for example, be an aromatic hydrocarbon group of from 6 to 14 carbon atoms such as phenyl, indenyl, naphthyl, phenanthrenyl or anthracenyl, and is preferably a phenyl group.

In the above-mentioned general formula (I), the "heteroaryl group" in Arom can, for example, be a 5 to 7-membered aromatic heterocyclic group containing from 1 to 4 sulphur atoms, oxygen atoms and/or nitrogen atoms such as furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl or pyrazinyl, and is preferably a pyridyl group.

In the above-mentioned general formula (I), the "$C_1$-$C_6$ alkyloxy group" in the "group α substituent groups" refers to an above-mentioned "$C_1$-$C_6$ alkyl group" bonded to an oxygen atom, and is, for example, a linear or branched alkoxy group of from 1 to 6 carbon atoms such as methoxy, ethoxy, propoxy, isopropoxy, butoxy, isobutoxy, s-butoxy, t-butoxy, pentyloxy, isopentyloxy, 2-methylbutoxy, neo-pentyloxy, hexyloxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy, and preferably a linear or branched alkoxy group of from 1 to 4 carbon atoms.

Preferred compounds represented by above-mentioned general formula (I) are compounds in which
1) $R^1$ is a hydrogen atom,
2) $R^2$ is a cyclopropyl group or methyl group,
3) A is a nitrogen atom,
4) D is an ethylene group, methylmethylene group or methylene group,
5) E is a group of formula CH or a methyl group-substituted carbon atom,
6) E is a group of formula CH,
7) Arom is a phenyl group or a halogen atom-substituted phenyl group,
8) Arom is a phenyl group, o-chlorophenyl group or o-fluorophenyl group,
9) Arom is a phenyl group, and
10)

----- is a single bond.

In the present invention, "central diseases" can include, for example, Alzheimer's disease, depression, Parkinson's disease, Huntington's chorea, Pick's disease, late dyskinesia, obsessive disorder and panic handicap, and refers particularly to Alzheimer's disease.

Another mode of the present invention is a method for the treatment of mammalian (particularly human) central diseases (particularly Alzheimer's disease), or Alzheimer's disease where microglia are activated (particularly where microglia are activated by β-amyloid), using a compound of above-mentioned general formula (I).

A further mode of the present invention is a method for suppressing microglia activation using a compound of above-mentioned general formula (I).

In yet another mode of the present invention, a compound of above-mentioned general formula (I) is used to produce a drug for central diseases (particularly Alzheimer's disease) or a drug for Alzheimer's disease where microglia are activated (particularly where microglia are activated by β-amyloid).

Specific examples of preferred compounds of above-mentioned general formula (I) are shown in Table 1 below. However, the inventive compounds are not limited to these. The abbreviations used in Table 1 below are as follows.

Me: methyl group
sb: single bond
db: double bond
cPr: cyclopropyl group
Ph: phenyl group

TABLE 1

(I)

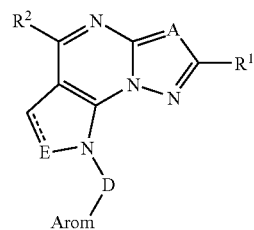

| Compound number | $R^1$ | $R^2$ | A | D | E | ----- | Arom |
|---|---|---|---|---|---|---|---|
| 1 | H | H | N | CH$_2$ | CH$_2$ | sb | Ph |
| 2 | H | Me | N | CH$_2$ | CH$_2$ | sb | Ph |
| 3 | H | cPr | N | CH$_2$ | CH$_2$ | sb | Ph |
| 4 | H | H | CH | CH$_2$ | CH$_2$ | sb | Ph |
| 5 | H | Me | CH | CH$_2$ | CH$_2$ | sb | Ph |
| 6 | H | cPr | CH | CH$_2$ | CH$_2$ | sb | Ph |
| 7 | H | H | N | (CH$_2$)$_2$ | CH$_2$ | sb | Ph |
| 8 | H | Me | N | (CH$_2$)$_2$ | CH$_2$ | sb | Ph |
| 9 | H | cPr | N | (CH$_2$)$_2$ | CH$_2$ | sb | Ph |
| 10 | H | H | CH | (CH$_2$)$_2$ | CH$_2$ | sb | Ph |
| 11 | H | Me | CH | (CH$_2$)$_2$ | CH$_2$ | sb | Ph |
| 12 | H | cPr | CH | (CH$_2$)$_2$ | CH$_2$ | sb | Ph |
| 13 | H | H | N | CH(Me) | CH$_2$ | sb | Ph |
| 14 | H | Me | N | CH(Me) | CH$_2$ | sb | Ph |

TABLE 1-continued (I)

| Compound number | R¹ | R² | A | D | E | | Arom |
|---|---|---|---|---|---|---|---|
| 15 | H | cPr | N | CH(Me) | CH₂ | sb | Ph |
| 16 | H | H | CH | CH(Me) | CH₂ | sb | Ph |
| 17 | H | Me | CH | CH(Me) | CH₂ | sb | Ph |
| 18 | H | cPr | CH | CH(Me) | CH₂ | sb | Ph |
| 19 | H | H | N | C(Me)₂ | CH₂ | sb | Ph |
| 20 | H | Me | N | C(Me)₂ | CH₂ | sb | Ph |
| 21 | H | cPr | N | C(Me)₂ | CH₂ | sb | Ph |
| 22 | H | H | CH | C(Me)₂ | CH₂ | sb | Ph |
| 23 | H | Me | CH | C(Me)₂ | CH₂ | sb | Ph |
| 24 | H | cPr | CH | C(Me)₂ | CH₂ | sb | Ph |
| 25 | H | H | N | CH₂ | CH(Me) | sb | Ph |
| 26 | H | Me | N | CH₂ | CH(Me) | sb | Ph |
| 27 | H | cPr | N | CH₂ | CH(Me) | sb | Ph |
| 28 | H | H | CH | CH₂ | CH(Me) | sb | Ph |
| 29 | H | Me | CH | CH₂ | OH(Me) | sb | Ph |
| 30 | H | cPr | CH | CH₂ | CH(Me) | sb | Ph |
| 31 | H | H | N | (CH₂)₂ | CH(Me) | sb | Ph |
| 32 | H | Me | N | (CH₂)₂ | CH(Me) | sb | Ph |
| 33 | H | cPr | N | (CH₂)₂ | CH(Me) | sb | Ph |
| 34 | H | H | CH | (CH₂)₂ | CH(Me) | sb | Ph |
| 35 | H | Me | CH | (CH₂)₂ | CH(Me) | sb | Ph |
| 36 | H | cPr | CH | (CH₂)₂ | CH(Me) | sb | Ph |
| 37 | H | H | N | CH(Me) | CH(Me) | sb | Ph |
| 38 | H | Me | N | CH(Me) | CH(Me) | sb | Ph |
| 39 | H | cPr | N | CH(Me) | CH(Me) | sb | Ph |
| 40 | H | H | CH | CH(Me) | CH(Me) | sb | Ph |
| 41 | H | Me | CH | CH(Me) | CH(Me) | sb | Ph |
| 42 | H | cPr | CH | CH(Me) | CH(Me) | sb | Ph |
| 43 | H | H | N | C(Me)₂ | CH(Me) | sb | Ph |
| 44 | H | Me | N | C(Me)₂ | CH(Me) | sb | Ph |
| 45 | H | cPr | N | C(Me)₂ | CH(Me) | sb | Ph |
| 46 | H | H | CH | C(Me)₂ | CH(Me) | sb | Ph |
| 47 | H | Me | CH | C(Me)₂ | CH(Me) | sb | Ph |
| 48 | H | cPr | CH | C(Me)₂ | CH(Me) | sb | Ph |
| 49 | H | H | N | CH₂ | CH₂ | sb | 2-Cl—Ph |
| 50 | H | Me | N | CH₂ | CH₂ | sb | 2-Cl—Ph |
| 51 | H | cPr | N | CH₂ | CH₂ | sb | 2-Cl—Ph |
| 52 | H | H | CH | CH₂ | CH₂ | sb | 2-Cl—Ph |
| 53 | H | Me | CH | CH₂ | CH₂ | sb | 2-Cl—Ph |
| 54 | H | cPr | CH | CH₂ | CH₂ | sb | 2-Cl—Ph |
| 55 | H | H | N | (CH₂)₂ | CH₂ | sb | 2-Cl—Ph |
| 56 | H | Me | N | (CH₂)₂ | CH₂ | sb | 2-Cl—Ph |
| 57 | H | cPr | N | (CH₂)₂ | CH₂ | sb | 2-Cl—Ph |
| 58 | H | H | CH | (CH₂)₂ | CH₂ | sb | 2-Cl—Ph |
| 59 | H | Me | CH | (CH₂)₂ | CH₂ | sb | 2-Cl—Ph |
| 60 | H | cPr | CH | (CH₂)₂ | CH₂ | sb | 2-Cl—Ph |
| 61 | H | H | N | CH(Me) | CH₂ | sb | 2-Cl—Ph |
| 62 | H | Me | N | CH(Me) | CH₂ | sb | 2-Cl—Ph |
| 63 | H | cPr | N | CH(Me) | CH₂ | sb | 2-Cl—Ph |
| 64 | H | H | CH | CH(Me) | CH₂ | sb | 2-Cl—Ph |
| 65 | H | Me | CH | CH(Me) | CH₂ | sb | 2-Cl—Ph |
| 66 | H | cPr | CH | CH(Me) | CH₂ | sb | 2-Cl—Ph |
| 67 | H | H | N | C(Me)₂ | CH₂ | sb | 2-Cl—Ph |
| 68 | H | Me | N | C(Me)₂ | CH₂ | sb | 2-Cl—Ph |
| 69 | H | cPr | N | C(Me)₂ | CH₂ | sb | 2-Cl—Ph |
| 70 | H | H | CH | C(Me)₂ | CH₂ | sb | 2-Cl—Ph |
| 71 | H | Me | CH | C(Me)₂ | CH₂ | sb | 2-Cl—Ph |
| 72 | H | cPr | CH | C(Me)₂ | CH₂ | sb | 2-Cl—Ph |
| 73 | H | H | N | CH₂ | CH(Me) | sb | 2-Cl—Ph |
| 74 | H | Me | N | CH₂ | CH(Me) | sb | 2-Cl—Ph |
| 75 | H | cPr | N | CH₂ | CH(Me) | sb | 2-Cl—Ph |
| 76 | H | H | CH | CH₂ | CH(Me) | sb | 2-Cl—Ph |
| 77 | H | Me | CH | CH₂ | CH(Me) | sb | 2-Cl—Ph |
| 78 | H | cPr | CH | CH₂ | CH(Me) | sb | 2-Cl—Ph |
| 79 | H | H | N | (CH₂)₂ | CH(Me) | sb | 2-Cl—Ph |
| 80 | H | Me | N | (CH₂)₂ | CH(Me) | sb | 2-Cl—Ph |
| 81 | H | cPr | N | (CH₂)₂ | CH(Me) | sb | 2-Cl—Ph |
| 82 | H | H | CH | (CH₂)₂ | CH(Me) | sb | 2-Cl—Ph |
| 83 | H | Me | CH | (CH₂)₂ | CH(Me) | sb | 2-Cl—Ph |
| 84 | H | cPr | CH | (CH₂)₂ | CH(Me) | sb | 2-Cl—Ph |
| 85 | H | H | N | CH(Me) | CH(Me) | sb | 2-Cl—Ph |
| 86 | H | Me | N | CH(Me) | CH(Me) | sb | 2-Cl—Ph |
| 87 | H | cPr | N | CH(Me) | CH(Me) | sb | 2-Cl—Ph |
| 88 | H | H | CH | CH(Me) | CH(Me) | sb | 2-Cl—Ph |
| 89 | H | Me | CH | CH(Me) | CH(Me) | sb | 2-Cl—Ph |
| 90 | H | cPr | CH | CH(Me) | CH(Me) | sb | 2-Cl—Ph |
| 91 | H | H | N | C(Me)₂ | CH(Me) | sb | 2-Cl—Ph |
| 92 | H | Me | N | C(Me)₂ | CH(Me) | sb | 2-Cl—Ph |
| 93 | H | cPr | N | C(Me)₂ | CH(Me) | sb | 2-Cl—Ph |
| 94 | H | H | CH | C(Me)₂ | CH(Me) | sb | 2-Cl—Ph |
| 95 | H | Me | CH | C(Me)₂ | CH(Me) | sb | 2-Cl—Ph |
| 96 | H | cPr | CH | C(Me)₂ | CH(Me) | sb | 2-Cl—Ph |
| 97 | H | H | N | CH₂ | CH | db | 2-Cl—Ph |
| 98 | H | Me | N | CH₂ | CH | db | 2-Cl—Ph |
| 99 | H | cPr | N | CH₂ | CH | db | 2-Cl—Ph |
| 100 | H | H | CH | CH₂ | CH | db | 2-Cl—Ph |
| 101 | H | Me | CH | CH₂ | CH | db | 2-Cl—Ph |
| 102 | H | cPr | CH | CH₂ | Cli | db | 2-Cl—Ph |
| 103 | H | H | N | (CH₂)₂ | CH | db | 2-Cl—Ph |
| 104 | H | Me | N | (CH₂)₂ | CH | db | 2-Cl—Ph |
| 105 | H | cPr | N | (CH₂)₂ | CH | db | 2-Cl—Ph |
| 106 | H | H | CH | (CH₂)₂ | CH | db | 2-Cl—Ph |
| 107 | H | Me | CH | (CH₂)₂ | CH | db | 2-Cl—Ph |
| 108 | H | cPr | CH | (CH₂)₂ | CH | db | 2-Cl—Ph |
| 109 | H | H | N | CH(Me) | CH | db | 2-Cl—Ph |
| 110 | H | Me | N | CH(Me) | CH | db | 2-Cl—Ph |
| 111 | H | cPr | N | CH(Me) | CH | db | 2-Cl—Ph |
| 112 | H | H | CH | CH(Me) | CH | db | 2-Cl—Ph |
| 113 | H | Me | CH | CH(Me) | CH | db | 2-Cl—Ph |
| 114 | H | cPr | CH | CH(Me) | CH | db | 2-Cl—Ph |
| 115 | H | H | N | C(Me)₂ | CH | db | 2-Cl—Ph |
| 116 | H | Me | N | C(Me)₂ | CH | db | 2-Cl—Ph |
| 117 | H | cPr | N | C(Me)₂ | CH | db | 2-Cl—Ph |
| 118 | H | H | CH | C(Me)₂ | CH | db | 2-Cl—Ph |
| 119 | H | Me | CH | C(Me)₂ | CH | db | 2-Cl—Ph |
| 120 | H | cPr | CH | C(Me)₂ | CH | db | 2-Cl—Ph |
| 121 | H | H | N | CH₂ | CH₂ | sb | 2-F—Ph |
| 122 | H | Me | N | CH₂ | CH₂ | sb | 2-F—Ph |
| 123 | H | cPr | N | CH₂ | CH₂ | sb | 2-F—Ph |
| 124 | H | H | CH | CH₂ | CH₂ | sb | 2-F—Ph |
| 125 | H | Me | CH | CH₂ | CH₂ | sb | 2-F—Ph |
| 126 | H | cPr | CH | CH₂ | CH₂ | sb | 2-F—Ph |
| 127 | H | H | N | (CH₂)₂ | CH₂ | sb | 2-F—Ph |
| 128 | H | Me | N | (CH₂)₂ | CH₂ | sb | 2-F—Ph |
| 129 | H | cPr | N | (CH₂)₂ | CH₂ | sb | 2-F—Ph |
| 130 | H | H | CH | (CH₂)₂ | CH₂ | sb | 2-F—Ph |
| 131 | H | Me | CH | (CH₂)₂ | CH₂ | sb | 2-F—Ph |
| 132 | H | cPr | CH | (CH₂)₂ | CH₂ | sb | 2-F—Ph |
| 133 | H | H | N | CH(Me) | CH₂ | sb | 2-F—Ph |
| 134 | H | Me | N | CH(Me) | CH₂ | sb | 2-F—Ph |
| 135 | H | cPr | N | CH(Me) | CH₂ | sb | 2-F—Ph |
| 136 | H | H | CH | CH(Me) | CH₂ | sb | 2-F—Ph |
| 137 | H | Me | CH | CH(Me) | CH₂ | sb | 2-F—Ph |
| 138 | H | cPr | CH | CH(Me) | CH₂ | sb | 2-F—Ph |

TABLE 1-continued (I)

Structure: R² and R¹ substituted pyrazolo fused ring system with E—N—D—Arom

| Compound number | R¹ | R² | A | D | E | | Arom |
|---|---|---|---|---|---|---|---|
| 139 | H | H | N | C(Me)₂ | CH₂ | sb | 2-F—Ph |
| 140 | H | Me | N | C(Me)₂ | CH₂ | sb | 2-F—Ph |
| 141 | H | cPr | N | C(Me)₂ | CH₂ | sb | 2-F—Ph |
| 142 | H | H | CH | C(Me)₂ | CH₂ | sb | 2-F—Ph |
| 143 | H | Me | CH | C(Me)₂ | CH₂ | sb | 2-F—Ph |
| 144 | H | cPr | CH | C(Me)₂ | CH₂ | sb | 2-F—Ph |
| 145 | H | H | N | CH₂ | CH(Me) | sb | 2-F—Ph |
| 146 | H | Me | N | CH₂ | CH(Me) | sb | 2-F—Ph |
| 147 | H | cPr | N | CH₂ | CH(Me) | sb | 2-F—Ph |
| 148 | H | H | CH | CH₂ | CH(Me) | sb | 2-F—Ph |
| 149 | H | Me | CH | CH₂ | CH(Me) | sb | 2-F—Ph |
| 150 | H | cPr | CH | CH₂ | CH(Me) | sb | 2-F—Ph |
| 151 | H | H | N | (CH₂)₂ | CH(Me) | sb | 2-F—Ph |
| 152 | H | Me | N | (CH₂)₂ | CH(Me) | sb | 2-F—Ph |
| 153 | H | cPr | N | (CH₂)₂ | CH(Me) | sb | 2-F—Ph |
| 154 | H | H | CH | (CH₂)₂ | CH(Me) | sb | 2-F—Ph |
| 155 | H | Me | CH | (CH₂)₂ | CH(Me) | sb | 2-F—Ph |
| 156 | H | cPr | CH | (CH₂)₂ | CH(Me) | sb | 2-F—Ph |
| 157 | H | H | N | CH(Me) | CH(Me) | sb | 2-F—Ph |
| 158 | H | Me | N | CH(Me) | CH(Me) | sb | 2-F—Ph |
| 159 | H | cPr | N | CH(Me) | CH(Me) | sb | 2-F—Ph |
| 160 | H | H | CH | CH(Me) | CH(Me) | sb | 2-F—Ph |
| 161 | H | Me | CH | CH(Me) | CH(Me) | sb | 2-F—Ph |
| 162 | H | cPr | CH | CH(Me) | CH(Me) | sb | 2-F—Ph |
| 163 | H | H | N | C(Me)₂ | CH(Me) | sb | 2-F—Ph |
| 164 | H | Me | N | C(Me)₂ | CH(Me) | sb | 2-F—Ph |
| 165 | H | cPr | N | C(Me)₂ | CH(Me) | sb | 2-F—Ph |
| 166 | H | H | CH | C(Me)₂ | CH(Me) | sb | 2-F—Ph |
| 167 | H | Me | CH | C(Me)₂ | CH(Me) | sb | 2-F—Ph |
| 168 | H | cPr | CH | C(Me)₂ | CH(Me) | sb | 2-F—Ph |
| 169 | Me | H | N | CH₂ | CH₂ | sb | Ph |
| 170 | Me | Me | N | CH₂ | CH₂ | sb | Ph |
| 171 | Me | cPr | N | CH₂ | CH₂ | sb | Ph |
| 172 | Me | H | CH | CH₂ | CH₂ | sb | Ph |
| 173 | Me | Me | CH | CH₂ | CH₂ | sb | Ph |
| 174 | Me | cPr | CH | CH₂ | CH₂ | sb | Ph |

Of the compounds shown above, compounds 2, 3, 5, 6, 8, 9, 14, 15, 20, 21, 26, 27, 32, 33, 38, 39, 44, 45, 50, 51, 56, 57, 62, 63, 68, 69, 74, 75, 80, 81, 86, 87, 92, 93, 98, 99, 104, 105, 110, 111, 116, 117, 122, 123, 128, 129, 134, 135, 140, 141, 146, 147, 152, 153, 158, 159, 164, 165, 170 and 171 are preferred; compounds 2, 5, 8, 9, 15, 21, 27, 33, 39, 45, 51, 57, 63, 69, 75, 81, 87, 93, 99, 105, 111, 117, 123, 129, 135, 141, 147, 153, 159 and 165 are more preferred; and compounds 2, 5, 8, 9, 14, 20, 50, 74, 98, 122 and 146 are yet more preferred.

The pharmacologically acceptable salts of inventive compounds of above-mentioned formula (I) are addition salts, for example, hydrohalides such as hydrofluoride, hydrochloride, hydrobromide and hydroiodide salts; inorganic acid salts such as nitrate, perchlorate, sulphate, phosphate salts and the like; salts of optionally fluorine atom-substituted lower alkanesulphonic acids, such as methanesulphonate, trifluoromethane-sulphonate and ethanesulphonate salts; arylsulphonic acid salts such as benzene sulphonate and p-toluenesulphonate salts; organic acid salts such as acetate, malate, fumarate, succinate, citrate, tartrate, oxalate and maleate salts; and amino acids salts such as salts of glycine, lysine, arginine, ornithine, glutamic acid and aspartic acid.

It should be noted that the inventive compounds (I) can also exist in solvated form, including as a hydrate, and the present invention includes these solvated forms.

Furthermore, the inventive compounds (I) can contain an asymmetric carbon, and in such cases the present invention includes the optical isomers, and isomer mixtures containing any proportion thereof.

The inventive compounds of above-mentioned formula (I) can easily be produced according to production methods disclosed in Japanese unexamined patents S51-141896 and H2-76880, and in J. Med. Chem. 1980, 23, 927-937; specifically, compound 9 can be produced as compound 68 of J. Med. Chem. 1980, 23, 927-937, compound 8 can be produced as in working example 45 of Japanese unexamined patent S51-141896, compound 14 can be produced as in working example 44 of Japanese unexamined patent S51-141896 and compound 2 can be produced as in working example 1 of Japanese unexamined patent H2-76880.

OPTIMUM MODE OF THE INVENTION

When inventive compounds of above-mentioned general formula (I) and pharmacologically acceptable salts thereof are used in medicine, particularly for the above-mentioned uses, they can be used as they are, or mixed with a suitable pharmacologically acceptable excipient or diluent, and can be administered orally as tablets, capsules, granules or a dispersion or syrup or the like, or non-orally as an injection agent, suppository, paste or agent for external use.

These preparations can be produced by known methods using additives such as excipients (for example, organic excipients such as: sugar derivatives such as lactose, saccharose, glucose, mannitol and sorbitol; starch derivatives such as cornstarch, potato starch, α-starch and dextrin; cellulose derivatives such as crystalline cellulose; gum arabic; dextran; pullalan; and inorganic excipients such as: silicate derivatives such as light anhydrous silicic acid, synthetic aluminium silicate, calcium silicate and magnesium metasilicate aluminate; phosphates such as calcium hydrogen phosphate; carbonates such as calcium carbonate and sulphates such as calcium sulphate), lubricants (for example, stearic acid and metal stearate salts such as calcium stearate and magnesium stearate; talc; colloidal silica; waxes such as beeswax and spermaceti; boric acid; adipic acid; sulphates such as sodium sulphate; glycol; fumaric acid; sodium benzoate; DL leucine; lauryl sulphates such as sodium lauryl sulphate and magnesium lauryl sulphate; silicic acids such as anhydrous silicic acid and silicic acid hydrate; and the above-mentioned starch derivatives), binders (for example, hydroxypropyl cellulose, hydroxypropyl methyl cellulose, polyvinylpyrrolidone and macrogol, and compounds similar to the above-mentioned excipients), disintegrating agents (for example, cellulose derivatives such as hydroxypropyl cellulose with a low degree of substitution, carboxymethyl cellulose, calcium carboxymethyl cellulose and internally cross-linked sodium carboxymethyl cellulose; and chemically modified starch-celluloses such as carboxymethyl starch, sodium carboxymethyl starch and cross-linked polyvinylpyrrolidone), emulsifiers (for example, colloidal clays such as bentonite and veegum; metal hydroxides such as magnesium hydroxide and aluminium hydroxide; anionic surfactants such as sodium lauryl sulphate and calcium stearate; cationic surfactants such as benzalkonium chloride; and non-ionic surfactants such as polyoxyethylene alkyl ether, polyoxyethylene sorbitan fatty acid ester and sucrose fatty acid ester), stabilisers (paraoxybenzoic acid esters such as methylparaben and propylparaben; alcohols such as chlorobutanol, benzyl alcohol and phenyl ethyl alcohol; benzalkonium chloride; phenols such as phenol and cresol; thimerosal; dehydroacetic acid; and sorbic acid), flavourings and perfumes (for example, commonly used sweeteners, acid flavourings, fragrances and the like) and diluents.

The dose depends on symptoms, age and the like, and usually for adults the minimum is 1 mg (preferably 5 mg) and the maximum is 1000 mg (preferably 500 mg) per administration, with from 1 to 6 administrations per day depending on the symptoms.

WORKING EXAMPLES

The following inventive compounds were used in the working examples below.

Compound 9 (henceforth referred to as "compound A"),
Compound 8 (henceforth referred to as "compound B"),
Compound 14 (henceforth referred to as "compound C"),
Compound 146 (henceforth referred to as "compound D"),
Compound 122 (henceforth referred to as "compound E"),
Compound 74 (henceforth referred to as "compound F"),
Compound 50 (henceforth referred to as "compound G"),
Compound 2 (henceforth referred to as "compound H"),
Compound 53 (henceforth referred to as "compound I"),
Compound 98 (henceforth referred to as "compound J"), and
Compound 20 (henceforth referred to as "compound K").

Compound A

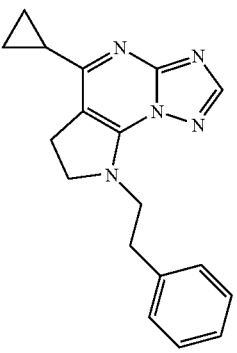

Compound B

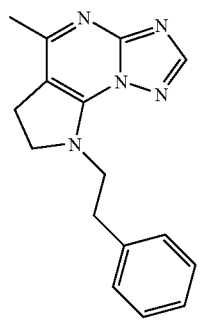

-continued

Compound C

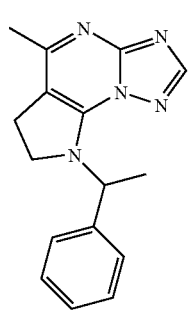

Compound D

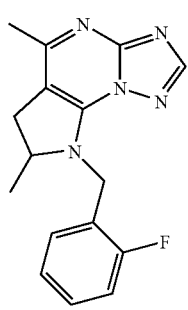

Compound E

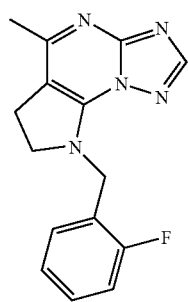

Compound F

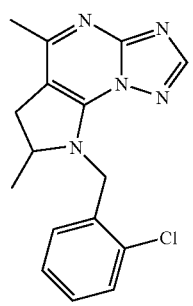

Compound G
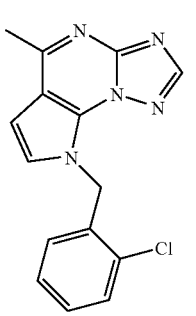

Compound H
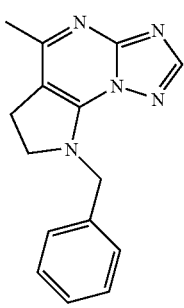

Compound I
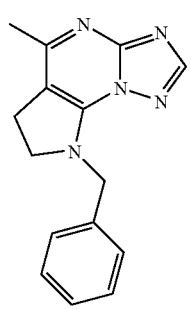

Compound J
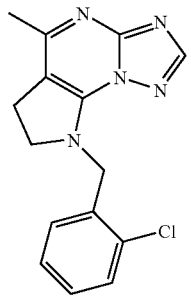

Compound K
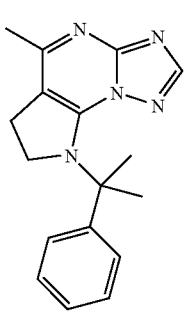

Working Example 1

Suppression of Microglia Activation Caused by β-Amyloid

Mouse abdominal cavity macrophages were prepared as follows for use as a model for microglia. A mouse (C3H/He, N, male, 7-10 weeks old: Nippon SLC) was subjected to cervical vertebrae dislocation then sprayed with 70% ethanol, the skin of the abdomen was cut open leaving the muscularis, from 5 to 7 ml of PBS (phosphate buffered saline) were injected into the abdominal cavity using a 24 G injection needle, the back was squeezed firmly, then injection solution was drawn from the abdominal cavity using a 23 G injection needle. The cells in the collected solution were centrifugally sedimented (900 rpm, 5 minutes) and washed using PBS, then $8 \times 10^4$/well were inoculated onto a 96-well microplate in culture solution (DMEM (Sigma), 10% FBS (Gibco), 100 U/ml penicillin+100 μg/ml streptomycin (Sigma)) and cultured in a 5% $CO_2$/95% air incubator at 37° C. The amount of nitrogen monoxide produced was taken as an indicator of macrophage activation. Specifically, the macrophages were incubated for 72 hours in the presence of 1) Aβ1-42 (20 μg/ml: Sigma), and 2) Aβ1-42 and the test compound, then 50 μl of Griess reagent (0.1% N-(1-naphthyl) ethylenediamine (Sigma), 1% sulphanilamide (Sigma), 3% H3PO4) were added to 50 μl of the supernatant, and the light absorbance at 570 nm was measured. It should be noted that this experiment was conducted in culture solution containing mouse interferon γ (250 U/ml: genzyme techne) and polymyxin B (10 μg/ml: Sigma). Also, the same operations were performed using zymosan A (140 ng/ml: Molecular Probes) or LPS (500 pg/ml: Sigma) instead of Aβ, as controls. For LPS, culture medium containing only mouse interferon γ was used.

The concentration when the absorbance in the presence of 2) Aβ and test compound was 50% of the absorbance when 1) only Aβ 1-42 was added was taken as $IC_{50}$, and the activity of the compound was appraised in terms of this value. The results are shown in Table 2 below.

TABLE 2

| Test compound | $IC_{50}$ (μg/ml) | | |
|---|---|---|---|
| | β-amyloid | zymosan A | LPS |
| Compound A | 0.4 | >5 | >5 |
| Compound B | 0.5 | >5 | >5 |
| Compound C | 0.4 | >5 | >5 |
| Compound D | 2.3 | >5 | >5 |
| Compound E | 3.2 | >5 | >5 |
| Compound F | 3.6 | >5 | >5 |
| Compound G | 3.8 | >5 | >5 |
| Compound H | 4.0 | >5 | >5 |
| Compound I | 4.3 | >5 | >5 |
| Compound J | 5.0 | >5 | >5 |
| Compound K | 5.0 | >5 | >5 |

As is clear from the table, the inventive compound selectively suppressed macrophage activity due to β-amyloid. The inventive compound is useful as a drug for Alzheimer's disease.

Working Example 2

Suppression of Neurocyte Death

Cerebellar granular cells were prepared as follows. The cerebellum of a rat (Wistar, 7 days old: Nippon SLC) was removed, papain-treated (9 U/ml, 15 minutes) to disperse the cells, then suspended in culture solution (MEM (Sigma), 20 mM KCl, 20 mM Hepes, 10% FBS (Gibco), 100 U/ml penicillin+100 μg/ml streptomycin (Sigma)). The prepared cerebellar granular cells were inoculated at $1.5 \times 10^5$ cells/well onto a 96-well microplate that had been coated beforehand with 25 μg/ml poly-L-lysine. The next day, AraC (10 μM: Sigma) was added, and on culture day 8, the system was supplied to the experiment. Abdominal cavity macrophages (prepared as in working example 1) were added to the culture day 8 cerebellar granular cells, and after 24 hours, Aβ 1-42 (20 μg/ml: Sigma) and test compound were added. After incubation for 72 hours, neurocyte death was measured. It should be noted that the experiment was conducted in culture solution containing mouse interferon γ (250 U/ml: genzyme techne) and polymyxin B (10 μg/ml: Sigma).

Post-culture cell death was determined by assaying free LDH (lactate dehydrogenation) activity using an LDH assay kit (Promega).

The concentration when cell death was 50% of that without the presence of test compound was taken as $IC_{50}$, and the neurocyte death-suppressive activity of the compound was appraised in terms of this value.

The results are shown in Table 3 below.

TABLE 3

| Test compound | $IC_{50}$ (μg/ml) |
|---|---|
| Compound $CH_2$ | 0.5 |

As is clear from the table, the inventive compound inhibited neurocyte death due to Aβ-induced macrophage activation. The inventive compound is useful as a drug for Alzheimer's disease.

PRODUCTION EXAMPLES

Production Example 1

Hard Capsules 100 mg of powdered compound A, 150 mg of lactose, 50 mg of cellulose and 6 mg of magnesium stearate are loaded into standard two-component type hard gelatin capsules to produce single unit capsules, which are then washed and dried.

Production Example 2

Soft Capsules

A mixture of compound B and digestible oil such as soya bean oil, cottonseed oil or olive oil is prepared and injected into gelatin using a direct exchange pump to obtain soft capsules containing 100 mg of active component, which are then washed and dried.

Production Example 3

Tablets

Tablets are prepared according to a common method using 100 mg of compound C, 0.2 mg of colloidal silicon dioxide, 5 mg of magnesium stearate, 275 mg of microcrystalline cellulose, 11 mg of starch and 98.8 mg of lactose. A coating is applied if desired.

Production Example 4

Suspension

A suspension is prepared such that 5 ml contains 100 mg of finely powdered compound D, 100 mg of sodium carboxymethyl cellulose, 5 mg of sodium benzoate, 1.0 g of sorbitol solution (Japan Pharmacopoeia) and 0.025 ml of vanillin.

Production Example 5

Cream

A cream is prepared by mixing 100 mg of finely powdered compound E into 5 g of cream comprising 40% white petrolatum, 3% microcrystalline wax, 10% lanolin, 5% Span 20, 0.3% Tween 20 and 41.7% water.

ADVANTAGES OF THE INVENTION

The invention of the present application has excellent activity and is useful as a drug for central diseases (particularly Alzheimer's disease) and as a drug for Alzheimer's disease where microglia are activated (particularly where microglia are activated by β-amyloid).

The invention claimed is:

1. A method for the treatment of central diseases selected from the group consisting of Alzheimer's disease, Parkinson's disease, Huntington's chorea and Pick's disease comprising administering a compound represented by general formula (I) below, or a pharmacologically acceptable salt thereof

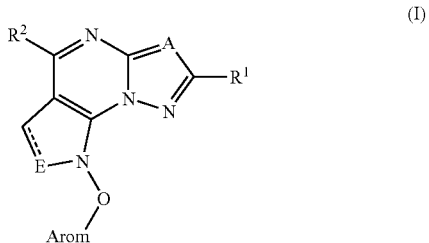

(I)

wherein:

$R^1$ represents a hydrogen atom, $R^2$ represents a $C_1$-$C_6$ alkyl group or $C_3$-$C_6$ cycloalkyl group, A represents a nitrogen atom, D represents a methylene group, a methyl methylene group, a halogen atom-substituted methylene group or a halogen atom substituted methyl methylene group, E represents a group of formula $Ch_2$, a group of formula $CHR^3$ (in the formula, $R^3$ represents a $C_1$-$C_6$ alkyl group), a group of formula CH or a $C_1$-$C_6$ alkyl group-substituted carbon atom, Arom represents an aryl group, an aryl group having from 1 to 3 identical or different substituent groups selected from the group consisting of halogen atoms, $C_1$-$C_6$ alkyl groups, and $C_1$-$C_6$ alkyloxy groups, a heteroaryl group or a heteroaryl group having from 1 to 3 substituent groups halogen atoms, $C_1$-$C_6$ alkyl groups, and $C_1$-$C_6$ alkyloxy groups, and the part represented by

----- is a single bond or double bond.

2. The method for treating central diseases selected from the group consisting of Alzheimer's disease, Parkinson's disease, Huntington's chorea and Pick's disease according to claim 1, wherein the aryl group of "Arom" is selected from the group consisting of phenyl, indenyl, naphthyl, phenanthrenyl, and anthracenyl, and the hetero aryl group of "Arom" is selected from the group consisting of furyl, thienyl, pyrrolyl, azepinyl, pyrazolyl, imidazolyl, oxazolyl, isoxazolyl, thiazolyl, tetrazolyl, thiadiazolyl, pyranyl, pyridyl, pyridazinyl, pyrimidinyl, and pyrazinyl.

3. The method for treating central diseases selected from the group consisting of Alzheimer's disease, Parkinson's disease, Huntington's chorea and Pick's disease according to claim 1, wherein "Arom" represents a phenyl group, a phenyl group having from 1 to 3 identical or different substituent groups selected from the group consisting of halogen atoms, $C_1$-$C_6$ alkyl groups, and $C_1$-$C_6$ alkyloxy groups, a pyridyl group or a pyridyl group having from 1 to 3 substituent groups selected from the group consisting of halogen atoms, $C_1$-$C_6$ alkyl groups, and $C_1$-$C_6$ alkyloxy groups.

4. The method for treating central diseases selected from the group consisting of Alzheimer's disease, Parkinson's disease, Huntington's chorea and Pick's disease according to claim 1, wherein "Arom" is a phenyl group, or a phenyl group having from 1 to 3 identical or different substituent groups chosen from "group a substituent groups" selected from the group consisting of halogen atoms, $C_1$-$C_6$ alkyl groups, and $C_1$-$C_6$ alkyloxy groups.

5. The method for treating central diseases selected from the group consisting of Alzheimer's disease, Parkinson's disease, Huntington's chorea and Pick's disease according to claim 1, wherein "Arom" is a phenyl group or a halogen atom substituted phenyl group.

6. The method for treating central diseases selected from the group consisting of Alzheimer's disease, Parkinson's disease, Huntington's chorea and Pick's disease according to claim 1, wherein E is a group of the formula CH or a methyl group substituted carbon atom.

7. The method for treating central diseases selected from the group consisting of Alzheimer's disease, Parkinson's disease, Huntington+s chorea and Pick's disease according to claim 1, wherein the part represented by

----- is a single bond.

8. The method of treatment of mammalian central diseases selected from the group consisting of Alzheimer's disease, Parkinson's disease, Huntington's chorea and Pick's disease according to claim 1 wherein the compound of the formula I is a compound of the formula (II)

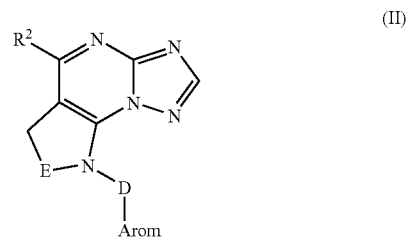

(II)

wherein:

$R^2$ is a cyclopropyl group or a methyl group;

D represents a methylene group, a methyl methylene group a halogen atom-substituted methylene group or a halogen atom substituted methyl methylene group;

E is a group of the formula OH or a methyl group substituted carbon atom

Arom is a phenyl group or a halogen atom substituted phenyl group;

or a pharmacologically acceptable salt thereof.

9. The method for treating central diseases selected from the group consisting of Alzheimer's disease, Parkinson's disease, Huntington's chorea and Pick's disease according to claim 1 wherein $R^2$ is a $C_{1-4}$ alkyl group.

10. The method for treating central diseases selected from the group consisting of Alzheimer's disease, Parkinson's disease, Huntington's chorea and Pick's disease according to claim 1 wherein $R^2$ is a methyl group.

11. The method for treating central diseases selected from the group consisting of Alzheimer's disease, Parkinson's disease, Huntington's chorea and Pick's disease according to claim 1, wherein the aryl group of "Arom" is an aromatic hydrocarbon group of from 6 to 14 carbon atoms and the hetero aryl group of "Arom" is a 5 to 7 membered aromatic heterocyclic group containing from 1 to 4 sulfur atoms, and/or nitrogen atoms.

12. The method for treating central diseases selected from the group consisting of Alzheimer's disease, Parkinson's disease, Huntington's chorea and Pick's disease according to claim 1 or claim 8, wherein the halogen atom of D is fluorine.

13. The method for treating central diseases selected from the group consisting of Alzheimer's disease, Parkinson's disease, Huntington's chorea and Pick's disease according to claim 1 or claim 8, wherein Arom is selected from the group consisting of a phenyl group, an O-chlorophenyl group and an O-fluorophenyl group.

14. A method for the treatment of central diseases selected from the group consisting of Alzheimer's disease, Parkinson's disease, Huntington's chorea and Pick's disease using a compound selected from the group consisting of

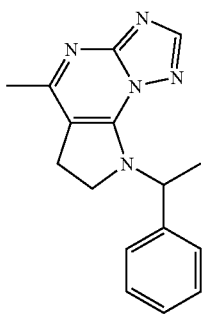 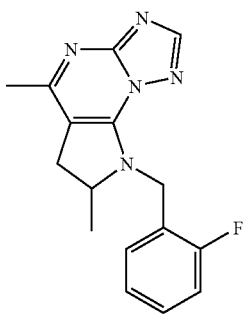 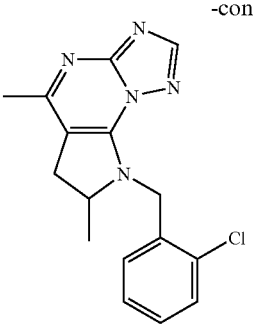 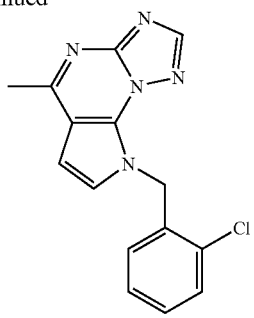
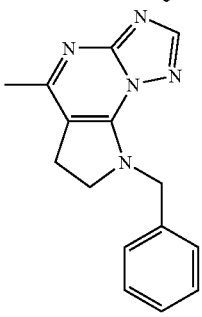 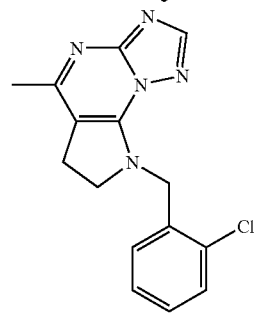
or a pharmacologically acceptable salt thereof.
* * * * *

UNITED STATES PATENT AND TRADEMARK OFFICE
CERTIFICATE OF CORRECTION

PATENT NO. : 7,425,559 B2 Page 1 of 3
APPLICATION NO. : 10/483674
DATED : September 16, 2008
INVENTOR(S) : Oda et al.

It is certified that error appears in the above-identified patent and that said Letters Patent is hereby corrected as shown below:

Front face of the patent, right hand column "(57) Abstract", please delete formula (I) as follows:
"

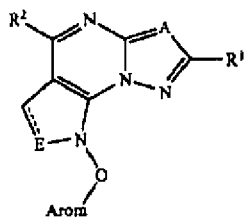

"

Front face of the patent, right hand column "(57) Abstract", please insert formula (I) as follows:
--

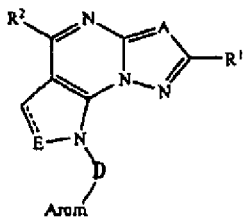

--

Column 2, line 25, please delete formula (I) as follows:
"

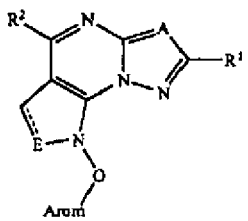

"

UNITED STATES PATENT AND TRADEMARK OFFICE
CERTIFICATE OF CORRECTION

PATENT NO.        : 7,425,559 B2
APPLICATION NO.   : 10/483674
DATED             : September 16, 2008
INVENTOR(S)       : Oda et al.

It is certified that error appears in the above-identified patent and that said Letters Patent is hereby corrected as shown below:

Column 2, line 25, please insert formula (I) as follows:
--
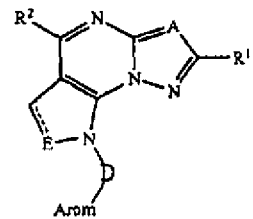
--

Column 11, Compound H, please delete as follows:
"
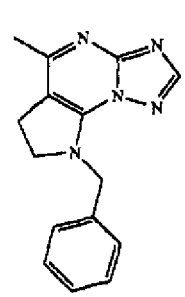
"

Column 11, Compound H, please insert as follows:
--
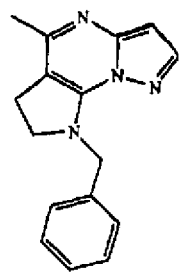
--

UNITED STATES PATENT AND TRADEMARK OFFICE
CERTIFICATE OF CORRECTION

PATENT NO. : 7,425,559 B2
APPLICATION NO. : 10/483674
DATED : September 16, 2008
INVENTOR(S) : Oda et al.

It is certified that error appears in the above-identified patent and that said Letters Patent is hereby corrected as shown below:

Column 14, claim 1 formula (I), please delete formula (I) as follows:
"
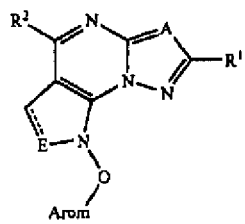
"

Column 14, claim 1 formula (I), please insert formula (I) as follows:
--
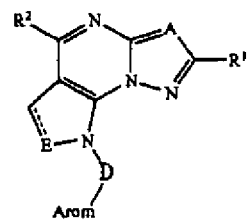
--

Column 14, line 59, after "formula", please delete "Ch$_2$," and insert as follows: --CH$_2$,--.

Signed and Sealed this

Fifteenth Day of September, 2009

David J. Kappos
*Director of the United States Patent and Trademark Office*